United States Patent [19]
Ullah et al.

[11] Patent Number: 5,880,106
[45] Date of Patent: Mar. 9, 1999

[54] ORAL DOSING FORMULATIONS OF DIDEOXY PURINE NUCLEOSIDES

[75] Inventors: Ismat Ullah, Cranbury; Shreeram Narahari Agharkar, Princeton; Gary James Wiley, Jackson, all of N.J.

[73] Assignee: Bristol-Myers Squibb Company, Princeton, N.J.

[21] Appl. No.: 942,660

[22] Filed: Oct. 2, 1997

Related U.S. Application Data

[63] Continuation-in-part of Ser. No. 882,204, May 13, 1992, abandoned, which is a continuation-in-part of Ser. No. 733,547, Jul. 22, 1991, abandoned.

[51] Int. Cl.$^6$ .................................................. A61K 31/70
[52] U.S. Cl. ............................ 514/45; 514/46; 536/27.14
[58] Field of Search ...................... 514/45, 46; 536/27.14

[56] References Cited

U.S. PATENT DOCUMENTS

| | | | |
|---|---|---|---|
| 4,260,596 | 4/1981 | Mackles | 424/14 |
| 4,786,505 | 11/1988 | Lovgren et al. | 424/81 |
| 4,861,759 | 8/1989 | Mitsuya et al. | 514/46 |
| 4,935,243 | 6/1990 | Borkan et al. | 424/441 |
| 5,026,687 | 6/1991 | Yarchoan et al. | 514/45 |
| 5,087,447 | 2/1992 | Rácz et al. | 424/81 |

FOREIGN PATENT DOCUMENTS

| | | |
|---|---|---|
| 0 138 540 | 4/1985 | European Pat. Off. . |
| 0138540 | 4/1985 | European Pat. Off. . |
| 2 082 456 | 3/1982 | United Kingdom . |
| 2082456 | 3/1982 | United Kingdom . |
| 8802629 | 4/1988 | WIPO . |
| 9109605 | 7/1991 | WIPO . |

OTHER PUBLICATIONS

Anderson, et al., International J. of Pharmaceutics, 1988, 45: 27–37.

Hoofnagle, et al., NTIS Publication PB89–186217, Method of Treatment of Hepatitis May 1989.

McGowan, et al., Reviews of Infect. Diseases, 1990, Overview of the Preclinical Devel. of an Antiretroviral Drug, 2',3'–Dideoxyinosine. 12 (Supplement 5) : S 513–S 521. (Jul.).

Dolin, et al., Reviews of Infect. Diseases, (1990) 12 Supp 5:S540–S549, 2',3'–Dideoxyinosine in Patients with AIDS or AIDS–Related Complex. (Jul.).

Hartman, et al., Clin. Pharmacol. Ther. (1991) 50: 278–285, II. The Effects of Different Oral Formulations and the Presence of Other Medications.

Anderson et al., "Preformulation Solubility and Kinetic Studies of 2',3'–Dideoxypurine Nucleosides: Potential Anti––AIDS Agents," *International Journal of Pharmaceutics*, 45, 27–37 (1988).

Hoofnagle et al., "Method of Treatment of Hepatitis," *NTIS Publication PB89–186217*, Specification of US Patent Application 07/351,502; Patent Application Filing Date—May 15, 1989.

McGowan et al., "Overview of the Preclinical Development of an Antiretroviral Drug, 2', 3'–Dideoxyinosine," *Reviews of Infectious Diseases*, 12(Suppl. 5), S513–S521 (Jul.–Aug. 1990).

Dolin et al., "2', 3'–Dideoxyinosine in Patients with AIDS or AIDS–Related Complex," *Reviews of Infectious Diseases*, 12(Suppl. 5), S540–S549 (Jul.–Aug. 1990).

Hartmann et al., "Pharmacokinetics of 2', 3'–Dideoxyinosine in Patients with Severe Human Immunodeficiency Infection. II. The Effects of Different Oral, Formulations and the Presence of Other Medications," *Clin. Pharmacol. Ther.*, 50(3), 278–285 (Sep. 1991).

Yarchoan et al.(II), "In Vivo Activity Against HIV and Favorable Toxicity Profile of 2', 3'–Dideoxyinosine," *Science*, 245, 412–415 (Jul. 28, 1989).

Rudnic et al., "Oral Dosage Forms," Ch. 89 in *Remington's Pharmaceutical Sciences, 18th Edition*, Gennaro et al.(eds.), Philadelphia College of Pharamcy and Science, Philadelphia, PA, 1990, only pp. 1633–1638 supplied.

*Primary Examiner*—Marian C. Knode
*Assistant Examiner*—L. Eric Crane
*Attorney, Agent, or Firm*—Richard P. Ryan

[57] ABSTRACT

Improved oral dosage formulations for acid-labile dideoxy purine nucleoside derivatives such as ddA, ddI, and ddG, have been developed by incorporating selected water-insoluble buffering systems in the formulation. These novel formulations provide reduced mass dosage units in the form of convenient, palatable chewable/dispersible tablets or a dry powder sachet. The reduced mass requirement, necessary to allow tablets of reasonable size, was achieved in part by an unexpected 20 to 25% increase in drug bioavailability resulting from use of the selected buffering systems comprised of an insoluble magnesium antacid agent and either dihydroxyaluminum sodium carbonate or calcium carbonate.

24 Claims, 1 Drawing Sheet

5,880,106

ORAL DOSING FORMULATIONS OF DIDEOXY PURINE NUCLEOSIDES

CROSS REFERENCE TO RELATED APPLICATION

This is a continuation-in-part application of U.S. Ser. No. 07/882,204 filed May 13, 1992 now abandoned, which is a continuation-in-part application of U.S. Ser. No. 07/733,547 filed on Jul. 22, 1991 and now abandoned.

BACKGROUND OF THE INVENTION

This invention relates to pharmaceutical compositions which provide convenient, palatable oral dosage formulations for the acid-labile dideoxy purine nucleosides such as 2',3'-dideoxyadinosine, 2'3'-dideoxyinosine, and 2',3'-dideoxyguanosine. More specifically, it relates to inclusion of specific antacid buffers which confer special advantages such as increased bioavailability, lower variability in bioavailability between patients, greater convenience, lessened potential for gastrointestinal distress, and higher patient acceptability.

Compositions containing 2',3'-dideoxyadenosine (ddA), 2'3'-dideoxyinosine (ddI), and 2'3'-dideoxyguanosine (ddG), and their triphosphates for treating retroviral infections have been disclosed. Mitsuya, et al., in U.S. Pat. No. 4,861,759 disclose the oral administration of these dideoxy purine nucleosides in the form of liquids or tablets containing antacid buffering agents so that the pH of the resultant composition is in the neutral (pH 6–pH 8) range. Specifically exemplified and claimed is an oral gavage formulation containing 0.1N acetate buffer with a pH of 6.8 to 7.2. Enteric coating of the tablets is also disclosed as an option.

The acid lability of the 2',3'-dideoxypurine nucleosides is well-known in the art and for that reason their oral administration typically requires administration on an empty stomach after ingestion of antacids. Prevention of acid-catalyzed hydrolysis of parent drug is important for these agents because their potent antiviral activity is lost in their hydrolysis by-products. Approaches to improving the acid stability of these acid-labile nucleoside derivatives have involved enteric-coated formulations, inclusion of a buffer in the pharmaceutical dosage form, and neutralization of the gastrointestinal tract just before drug ingestion by pretreatment with commercial antacids such as Maalox® or Mylanta®. Studies reported by McGowan, et al. in *Reviews of Infectious Diseases*, Vol. 12, Supp. 5, 5513–521 (1990) indicated that for ddI a superior approach for oral administration involves formulation of the drug at selected dose levels in combination with a fixed amount of citrate-phosphate buffer as a powder mixture. This dry mixture is enclosed in foil to provide a sachet (the "CP sachet") that must be mixed and diluted with liquid before oral ingestion.

Formulation approaches involving enteric coatings were not promising. Enteric coatings tended to reduce the nucleoside drug's bioavailability and depress peak plasma levels. High peak plasma levels of active drug are an important requirement for its clinical antiviral activity. Enteric coated formulations also were especially susceptible to a meal effect, further reducing bioavailability.

The citrate-phosphate buffered ddI formulations, which allow oral dosing, were preferred clinically for long-term therapy over the earlier available lyophilized dosage form of the drug which requires reconstitution prior to intravenous administration. These oral powder formulations for reconstitution consist of varying ddI levels combined with the same amount of buffering ingredients (about 10 g per day) regardless of final drug dose strength. All dose strength formulations thus have the same acid neutralization capacity. However, the powder blend sachets are bulky (about 20 g/dose) and inconvenient - their use causes some patient inconvenience. Reconstitution is always required prior to administration and results in a large volume of constituted solution (due to 20 g of solute) to be ingested. This salty solution can cause diarrhea and the required ingestion of about 10 g per day of soluble antacid buffers may result in systemic alkalosis when administered on a long-term basis as required, for example, in treating HIV infections.

A comparison of available oral formulations of ddI was recently reported (Hartman, et al., "Pharmacokinetics of 2',3'-dideoxyinosine in patients with severe human immunodeficiency infection. II. The effects of different oral formulations and the presence of other medications," *Cli. Pharmacol. Ther.*, 1991; 50:278–85). With the maximum bioavailability of any buffered preparation being reported as $\leq 40\%$, the reference concludes that "an optimal preparation remains to be found." Of existing formulations, the "CP sachet" appeared to be the best oral preparation although its use caused reported diarrhea and/or hypokalemia in some patients.

It was an object of the present invention to provide pharmaceutical compositions for these acid-labile nucleoside derivatives which would allow convenient oral administration of reduced mass dosage formulations such as tablets which could be chewed and swallowed or readily dispersed in liquid for ingestion. Such a composition would also allow formulation of reduced mass sachet dosage forms.

Another objective was to find a combination of antacid buffers effective in preventing acid hydrolysis of the nucleosidic agent but whose effect on diarrhea and/or electrolyte and pH imbalances would be minimized.

A further object of the invention was to provide a pleasant tasting composition with high levels of patient acceptance and tolerability. A key to realization of these objects was in providing in a reduced mass form the same amount of bioavailable drug delivered by the bulky dry powder blend provided in the citrate-phosphate buffer sachets. Surprisingly, improved buffer systems comprising certain water-insoluble aluminum or calcium carbonates in combination with water-insoluble magnesium antacids were found to increase drug bioavailability by about 20 to 25%. Addition of reduced amounts of compatible sweetening and flavoring agents for incorporation into the improved drug-buffer composition also contributed to achieving the objects of the invention.

SUMMARY DESCRIPTION OF THE INVENTION

Improved pharmaceutical compositions have been discovered which allow the oral administration of the acid-labile dideoxy purine nucleoside derivatives in the form of reduced mass powder sachets and preferably as convenient palatable oral tablets. These tablets are also readily dispersible in liquids to offer an optional route of ingestion. The crux of the present invention lies in the unobvious selection of certain water-insoluble antacids to provide the unique buffering action, allowing reduced mass of the formulation while providing increased bioavailability, enhanced palatability and decreased gastrointestinal side-effects. Successful tablet formulation resulted from selection and development of compatible water-insoluble antacid buffer systems, which when combined with sweetening agents, flavoring agents, and other optional excipients deliver drug at a higher bioavailability than realizable in previous oral formulations, thereby permitting presentation in the more convenient and acceptable reduced mass form of a sachet or a chewable/dispersible tablet.

DETAILED DESCRIPTION OF THE INVENTION

Figure 1:
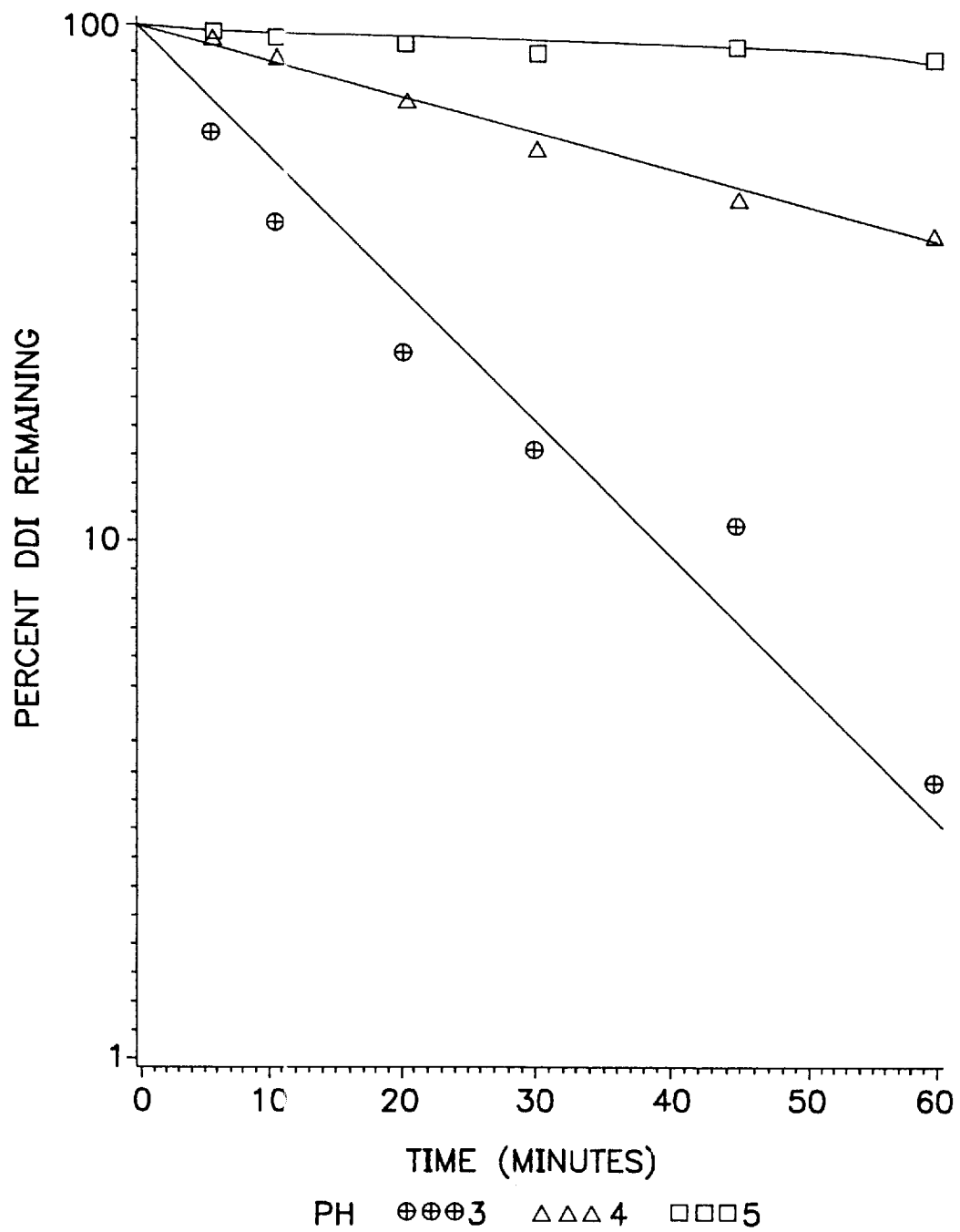
FIG. 1 discloses a semi-logithmic plot of the degradation of Didanosine (ddI) as a function of pH and time at 37° C.

The present invention concerns an improvement in oral dosage formulations of acid-labile dideoxy purine nucleoside derivatives, e.g. ddA, ddI, and ddG. This formulation improvement concerns incorporation of the active drug ingredient in a reduced mass acid buffer formulation which can be provided as convenient palatable tablets that can be chewed and swallowed or easily dispersed in appropriate non-acidic liquids and then ingested. Reduced mass powder formulations in sachet form are also intended.

In order to formulate these acid-labile drugs as reasonably-sized convenient chewable/dispersible tablets, a pharmaceutical composition was required that would provide sufficient bioavailable drug in a palatable but non-bulky form. It was discovered that use of certain insoluble antacid buffers in combination gave a buffer system which actually provided an increase of drug bioavailability with reduced variability between human subjects, compared with previous oral formulations. The improved antacid buffering performance of the insoluble antacid agents/combinations of the present invention is surprising in that it does not depend simply on "buffering capacity" which can be calculated stoichimetrically. Compared to previously used dideoxynucleoside-buffer systems, smaller amounts of the new systems provided increased bioavailability of the dideoxynucleoside such as ddI. In addition, the new combination antacid buffer systems have improved palatability thereby making possible the use of reduced amounts of sweetening and flavoring agents, further contributing to the reduction in formulation weight. Use of the new antacid buffers also result in a lowered potential for diarrhea or constipation which commonly result from chronic administration of many antacid agents.

The term "water-insoluble buffers," as applied to antacid agents which may be used in the instant buffer system, include antacids which have low water solubility as well as those which are generally insoluble. The combination buffer systems of this invention are, in general, comprised of mixtures of water-insoluble antacid magnesium compounds with dihydroxyaluminum alkali metal carbonates or calcium carbonate. Preferred mixtures comprise about one part of a water-insoluble antacid magnesium compound in combination with about 2 to 4 parts of a dihydroxyaluminum alkali metal carbonate or with about 1.5 to 3 parts of calcium carbonate which is most preferred.

The water-insoluble antacid magnesium compound can be selected from magnesium carbonate, magnesium carbonate hydroxide, magnesium hydroxide, magnesium oxide, magnesium phosphate (tribasic), and magnesium trisilicate; or a combination of these to comprise the magnesium antacid component. Magnesium oxide and magnesium hydroxide are preferred, with magnesium hydroxide being the most preferred compound. The dihydroxyaluminum alkali metal carbonates refer chiefly to dihydroxyaluminum potassium carbonate and dihydroxyaluminum sodium carbonate, which is preferred.

The present invention was developed in part by employing an in vitro model of a gastric system to measure acid neutralization. While the acid neutralization capacity can be readily calculated and measured using standard titration procedures, it is the rate of neutralization and maintenance-stability of the pH value that is of paramount importance with respect to nucleosidic drug stability.

The range of ratios of the insoluble aluminum and calcium antacid buffer agents, such as dihydroxyaluminum alkali metal carbonate and calcium carbonate, to the insoluble magnesium antacid buffer agent also reflects a balance between the diarrhea-promoting characteristics of the magnesium component and the constipation-causing characteristics of the aluminum and calcium components. Additionally, the instant combinations provide superior acid neutralizing properties which are very important given the limited quantities of buffer that can be used due to weight restrictions for tablet formulations.

Another feature of the improved combination antacid buffer systems concerns the resultant gastric acidity following administration. For the dideoxy purine nucleosides, a pH of about 5 would appear to be the lower limit below which the drugs undergo rapid acid-catalyzed hydrolysis. A desirable buffer system would therefore maintain the stomach pH above 5 for at least half an hour but preferably for about an hour. It is also desirable, as achieved with these new buffer systems, that the stomach pH not rise much above 5 in order to limit the potential for physiologic pH imbalance (alkalosis) in the gastrointestinal tract. The combination antacid buffer systems of the present invention were selected initially using an acid neutralization rate test which will be described in greater detail infra. It is well known that strongly basic compounds can give rise to GI alkalosis with repeated ingestion.

The unique synergistic characteristics of the selected insoluble aluminum and/or calcium carbonate compounds of the new combination buffer systems are demonstrated by the results obtained when aluminum hydroxide, a widely-used antacid, was substituted for the selected aluminum/calcium component of the new buffer combinations. The aluminum hydroxide-containing buffer system was inferior to the instant buffer systems as it gave increased acidic pH values when studied in an in vitro gastric secretion test, even when additional aluminum hydroxide suspension was added. In contrast, the use of dihydroxyaluminum sodium carbonate or calcium carbonate combined with an insoluble magnesium compound gave time extended pH values in the desired range (above pH 5 but not strongly basic) when studied in the in vitro gastric secretion system, indicative of its more efficient acid neutralization. This also demonstrates that simple neutralization equivalency will not distinguish between antacid agents insofar as the desired performance is concerned.

In some of the instant formulations a water-soluble antacid buffer, such as a phosphate or citrate salt such as sodium citrate, may also be added. These soluble antacid buffers would be provided in a lesser amount, generally representing less than about a quarter of the total amount of buffer. In general, only the water-insoluble buffer systems are preferred.

Finally, the importance of the new improved combination buffer systems can be appreciated in terms of improved palatability. Selection of the insoluble antacid buffers comprising these novel pharmaceutical compositions provide superior acid neutralization capacity while having organoleptic properties which minimize the amounts of sweetening and flavoring agents required for palatability. In this way formulation weight is kept low as only small amounts of sweetening and flavoring ingredients are necessary to meet taste acceptance.

In similar fashion, as for the previous citrate-phosphate buffer dry powder sachet formulations, the water-insoluble antacid buffers are provided at a constant level, independent of the drug dose to be incorporated in the instant pharmaceutical compositions. The improved buffer systems of the new formulations reduce the total amount of antacid ingested daily (about 10 g) in prior clinical formulations to a range of about 3 to 8 g daily in the reduced mass formulations, either sachets or chewable dispersible tablets at recommended dose levels. This reduction in daily antacid intake is beneficial to the GI system.

Due to the increased bioavailability of drug substance achieved in these new pharmaceutical compositions, less drug may be used to give potencies equivalent to the previous "CP sachet" sachet dosage forms. Clinical studies conducted with ddI demonstrated the bioavailability advantage for the new formulations. As can be seen, two tablets formulated from the improved pharmaceutical compositions can be given in place of a sachet dose as shown in Table 1. The increased bioavailability of the drug substance also contributes to lower tablet weight.

Table 1

Dose Equivalencies of ddI Chewable/Dispersible Tablets to Citrate/Phosphate Buffer Sachets Two 150 mg ddI tablets (300 mg) equivalent to a 375 mg sachet.
Two 100 mg ddI tablets (200 mg) equivalent to a 250 mg sachet.
Two 50 mg ddI tablets (100 mg) equivalent to a 167 mg sachet.
Three 25 mg ddI tablets (75 mg) equivalent to a 100 mg sachet.

As shown in Table 1, the dose weight of ddI may be reduced by about 20–25% when given in the new chewable/dispersible tablet formulations compared to the old "CP" sachet form.

The improved oral pharmaceutical compositions of this invention contain then from about 5 to 375 mg of a 2',3'-dideoxy purine nucleoside derivative such as ddA, ddI, and ddG per tablet and from about 10 to 375 mg per sachet unit. There is also provided in these compositions, sufficient antacid buffer, generally in the range of about 800 to 2800 mg, comprised of a water-insoluble antacid magnesium compound in combination with a dihydroxyaluminum alkali metal carbonate or calcium carbonate; so that adequate antacid capacity is achieved by the ingestion of two tablets or one reduced mass sachet as a per dose. Desired sweetener agent, flavor and tableting excipients may be incorporated. More detailed specification of the mixed water-insoluble antacid buffer systems as well as other ingredients that may be incorporated into these novel dideoxy nucleosidic pharmaceutical compositions is given in the specific embodiments described infra.

Another aspect of the present invention concerns the palatability of the oral tablet formulation. The taste characteristics of the water-insoluble antacid buffers selected for use in the present invention are such that their incorporation into the present pharmaceutical compositions facilitates the objective of tablet palatability by reducing the demand for ingredients to mask the taste of the buffer system itself. A sweetener component was selected which is comprised of aspartame to which sucrose or sorbital may be optionally added to enhance the palatability according to the specific antacid compounds selected for the final composition. In general, little if any sucrose is added when calcium carbonate is selected as an antacid buffer component. From about 2 to 5 parts of sucrose per part of aspartame is preferred when dihydroxyaluminum sodium carbonate is an ingredient.

Selection of flavoring agents also may be varied depending upon the specific antacid compounds being used. Taste tests were employed to obtain the best tasting flavored compositions. Wintergreen, orange and mandarin orange flavorings are preferred.

Other pharmaceutical additives may also be incorporated. Although traditional chewable tablets do not require a disintegrant, one may be incorporated into these compositions in order to insure rapid disintegration when dosing as a dispersion is intended, as well as a rapid rate of acid neutralization after oral administration. Commercial disintegrants such as Polyplasdone XL and Explotab may be used. Glidants, such as silicon dioxide, and lubricants, such as magnesium stearate, may also be incorporated optionally into the pharmaceutical compositions of the present invention. The use of these and other pharmaceutical excipients is well known in the art. Similarly the formulation process and tableting operations would be considered standard practice in the pharmaceutical art.

For clinical use, two chewable/dispersible tablets, having the selected strengths of drug per tablet deemed appropriate by the attending or prescribing medical practitioner, will be chewed thoroughly either together or in rapid succession. A rinse of about 4 oz. (120 ml) of non-acidic liquid such as water may also be given. Alternatively, the two tablets may be thoroughly dispersed in at least one ounce of water and the dispersion then taken orally. To improve palatability and/or provide a taste change, the aqueous dispersion can be doubled or tripled in volume by the addition of another liquid such as milk, flavored milk, or a fruit juice. These mixed dispersions may be stored for up to an hour at room temperature prior to ingestion.

The tablets or dispersion may be given once or twice daily and preferably be ingested on an empty stomach twice daily. This means at least 30 minutes before eating or 2 hours after eating. This dosing regimen is offered as a guide to clinical use with the realization that the practice of medicine is individualized and medical practitioners may depart from this general guide according to their treatment practice with individual patients. Similarly the level of drug to be administered will be that which the medical practitioner feels is appropriate for the patient being treated, taking into account severity of disease, age and condition of patient and other relevant medical parameters.

In summary, the improved pharmaceutical compositions developed for oral administration of the acid-labile dideoxy purine nucleosides give reduced weight dosage formulations with unexpectedly improved drug bioavailability, lower variability between patients, and with better palatability relative to prior formulations. These characteristics allow the formulation of reduced mass sachets and chewable/dispersible tablet formulations with their increased convenience and patient preference. The greater patient convenience associated with the use of oral tablets is felt to have a beneficial effect on patient compliance with their drug regimen. To patients that might have problems in chewing or swallowing, the dispersibility of the tablets is a further advantage.

The following examples describe in detail test methods and procedures for preparation of pharmaceutical compositions and formulations of the present invention. It will be apparent to those skilled in the art that many modifications, both of methods and materials and amounts, may be practiced without departing from the purpose and intent of this disclosure. From the foregoing description and the following examples it is believed that one skilled in the art is able to use the invention to the fullest extent.

EXAMPLE 1

Acid Neutralization Rate—Test Method

This test was developed to determine rate and duration of acid neutralization and to measure efficiency of the formulations to maintain the desired pH. This test was performed using a USP apparatus 11 dissolution assembly (paddle method). Into the dissolution vessel, 750 mL of purified water, USP was added and equilibrated to 37°±1° C. Into this water, a calibrated pH probe was immersed, and 4.0 mL of 1.0N HCl was added, and the paddle stirrer, set at 100 RPM, was started. The contents were allowed to stir for at least two minutes before addition of the test sample. Test samples were prepared by dissolving/dispersing the test sample in a sufficient volume of water. A Harvard Infusion/Withdrawal Pump (model 940) was set up with a 30 mL syringe filled with 0.8214N HCl. The piston speed was adjusted to deliver 28 mL of solution per hour (23 mEq/hour). The test sample was added to the dissolution flask and the Harvard pump was started immediately. The solution container was rinsed with purified water, USP, and the volume was made to 972 mL. The media pH was recorded at selected time intervals over a period of one hour.

Compositions and Formulations

The following examples of pharmaceutical compositions and formulations employ ddI (generically known as Didanosine) as the representative drug member of the acid-labile nucleosides. This is because ddI has been approved for use in treating AIDS patients. The other acid-labile nucleosidic drug agents, e.g. ddA and ddG, could be readily substituted for ddI in the compositions and formulations.

The pharmaceutical compositions comprise, as a powder blend, didanosine and a buffer system which is itself comprised of an insoluble magnesium antacid compound, e.g. magnesium hydroxide, combined with either calcium carbonate or an insoluble aluminum antacid compound, e.g. dihydroxyaluminum sodium carbonate. Sweeteners, flavors, and other desirable excipients used in powder blends, as well as a water-soluble antacid, e.g. sodium citrate, may also be components. These pharmaceutical compositions are then formulated into oral dosing forms such as an oral powder suspension or chewable/dispersible tablets.

EXAMPLE 2

Oral Suspension Dosage Form (reduced mass sachet)

A preferred embodiment of a didanosine powder composition for an oral suspension dosage form is prepared as follows.

The following ingredients were weighed:

| Ingredient | Weight |
| --- | --- |
| didanosine | 7.6 Kg |
| magnesium hydroxide | 14.0 Kg |
| dihydroxyaluminum sodium carbonate | 42.0 Kg |
| sodium citrate dihydrate | 12.0 Kg |
| sucrose powder | 43.0 Kg |
| orange flavor | 1.2 Kg |

All ingredients are added in a tumbling type V-blender and then blended for 15 minutes. The blend is then milled through Fitzmill with hammers forward using #00 plate at medium chamber speed and medium feed rate. The milled material is blended again in tumbling type V-blender for 20 minutes. This bulk blend is then assayed for drug potency and content uniformity (found 378 mg didanosine/6.0 g powder weight and RSD of 0.9% for 10 samples with a range of 369.8 mg to 381 mg/6.0 g weight) and filled into unit dose foil packets using a Bartelt powder filling and sealing machine (model IMG-9). These foil packets will contain 6.0 g of didanosine oral suspension powder which can have the following compositions (depending on desired drug strength).

| Ingredient | Weight |
| --- | --- |
| didanosine | 0.005 g to 0.375 g |
| magnesium hydroxide | 0.700 g |
| dihydroxyaluminum sodium carbonate | 2.100 g |
| sodium citrate dihydrate | 0.600 g |
| sucrose powder | Q.S. |
| orange flavor | 0.060 g |
| Net Weight | 6.000 g* |

*Prior Art sachets contain 20 g of powder blend.

*Prior Art sachets contain 20 g of powder blend.

EXAMPLE 3

Chewable/Dispersible Oral Tablet

An embodiment of a didanosine chewable/ dispersible tablet formulation is prepared as follows.

The following ingredients were weighed:

| Ingredient | Weight |
| --- | --- |
| didanosine | 2.083 Kg |
| magnesium hydroxide | 7.500 Kg |
| dihydroxyaluminum sodium carbonate | 22.500 Kg |
| sodium citrate dihydrate | 5.000 Kg |
| aspartame | 0.667 Kg |
| polyplasdone XL10 | 1.250 Kg |
| powdered sucrose | 2.667 Kg |
| microcrystalline cellulose pH 101 | 6.500 Kg |
| silicon dioxide | 0.625 Kg |
| natural wintergreen flavor | 0.375 Kg |
| magnesium stearate (for compaction) | 0.625 Kg |

All ingredients are placed in a tumbling type V-blender and blended for 10 minutes. The blend is then milled through Fitzmill with knives forward, using 1 B plate at medium chamber speed, and medium feed rate. The milled material is blended again in tumbling type V-blender for 10 minutes. The blend is slugged on twelve station Colton D3 tablet press. The slugs are milled through Fitzmill with knives forward, using #4 plate at slow chamber speed, and medium feed rate. The milled slugs are then passed through oscillators using 16 mesh wire screen. The resulting granules are placed in a tumbling type V-blender to which calculated amount of magnesium stearate 0.0125 g/2.9875 g of granulation weight, and blended for 7 minutes. This blend is then assayed for drug potency and content uniformity (found 126 mg didanosine/ 3.0 g granulation weight and RSD of 1.0% for 10 samples with a range of 124 mg to 128 mg/3.0 g granulation weight. The granulation is compacted into tablets on twelve station D3 rotary tablet press using ⅞" round, flat beveled edge punches. Tablets are compacted to hardness of 16–24 Strong Cobb Units to a target weight of 3.0 g/tablet.

These tablet formulations then have the following compositions (depending on desired drug strength).

| Ingredient | Weight |
|---|---|
| didanosine | 0.005 g to 0.375 g |
| magnesium hydroxide | 0.4500 g |
| dihydroxyaluminum sodium carbonate | 1.3500 g |
| sodium citrate dihydrate | 0.3000 g |
| aspartame | 0.0400 g* |
| polyplasdone XL10 | 0.0750 g |
| powdered sucrose | 0.1600 g |
| microcrystalline cellulose pH 101 | Q.S. |
| silicon dioxide | 0.0375 g |
| natural wintergreen flavor | 0.0225 g |
| magnesium stearate (for compaction) | 0.0375 g |
| magnesium stearate (for tableting) | 0.0125 g |
| Net Weight | 3.00 g |

*0.0600 g aspartame to be used for 150 mg and higher strength didanosine tablets.

EXAMPLE 4

Aluminum, Sodium and Sugar Free Chewable/ Dispersible Oral Tablet

A preferred embodiment of an aluminum, sodium and sugar free didanosine chewable/dispersible tablet formulation is prepared as follows.

| Ingredient | Weight |
|---|---|
| didanosine | 0.300 Kg |
| calcium carbonate | 1.100 Kg |
| magnesium hydroxide | 0.500 Kg |
| aspartame | 0.120 Kg |
| polyplasdone XL10 | 0.150 Kg |
| silicon dioxide | 0.040 Kg |
| microcrystalline cellulose | 1.460 Kg |
| natural orange flavor | 0.100 Kg |
| magnesium stearate (for slugging) | 0.020 Kg |
| magnesium stearate (for tableting) | 0.010 Kg |

All ingredients are placed in a tumbling V-blender and blended for 10 minutes. The blend is then milled through Fitzmill with knives forward using #1 plate at medium chamber speed, and medium feed rate. The milled material is blended again in tumbling type V-blender for 10 minutes. The blend is slugged on single punch F-press. The slugs are milled through Fitzmill with knives forward, using #4 plate at slow chamber speed, and medium feed rate. The milled slugs are then passed through oscillator using 16 mesh wire screen. The resulting granules are placed in a tumbling type V-blender to which calculated amount of magnesium stearate 0.01 g/1.89 g of granulation weight and blended for 10 minutes. The blend is then compacted into tablets on single punch F-press using ¾" round, flat beveled edge punches. Tablets are compacted to hardness of 18–21 strong cell units to a target weight of 1.9 g/tablet.

As an example, tablet formulations have the following composition.

| Ingredient | Amount (g) Per Tablet |
|---|---|
| didanosine | 0.005 to 0.375 |
| calcium carbonate (light) | 0.550 |
| magnesium hydroxide | 0.250 |
| aspartame | 0.020 to 0.060* |
| polyplasdone XL10 | 0.075 |
| silicon dioxide | 0.020 |
| microcrystalline cellulose | q.s. |
| natural orange flavor | 0.050 |
| magnesium stearate (for slugging) | 0.010 |
| magnesium stearate (for tableting) | 0.005 |
| Total Tablet Weight | 1.900 |

*Amount of aspartame can vary with didanosine content and intermediate strength compositions contain proportional amounts of aspartame.

EXAMPLE 5

Chewable/Dispersible Oral Tablet #2

A more preferred embodiment of a didanosine chewable/dispersible tablet formulation can be prepared by appropriate modification of the procedure set forth in Example 4 to provide tablets having the following composition.

| Ingredient | Amount (g) Per Tablet |
|---|---|
| didanosine | 0.005 to 0.375 |
| calcium carbonate (light) | 0.550 |
| magnesium hydroxide | 0.250 |
| aspartame | 0.020 to 0.070* |
| polyplasdone XL10 | 0.100 |
| sorbitol | 0.300 |
| microcrystalline cellulose | q.s. |
| mandarin orange flavor | 0.050 |
| magnesium stearate (for slugging) | 0.015 |
| magnesium stearate (for tableting) | 0.015 |
| Total Tablet Weight | 2.100 |

*Amount of aspartame can vary with didanosine content.

EXAMPLE 6

Evaluation of the Comparative Bioavailability of Didanosine Administration of 375 mg Dose as a Solution, Chewable Tablet and Suspension Assessment of bioavailabilities of didanosine from two new formulations, a chewable tablet and a suspension, relative to that of a citrate/phosphate buffer solution, was conducted in 18 male subjects who were seropositive for the Human Immunodeficiency Virus (HIV). This study was performed in six subjects at each of the three clinical sites using an open randomized three-way crossover design. Each subject received a single 375 mg didanosine oral dose after an overnight fast. There was a 7-day washout period between each treatment. Serial blood samples and the total urinary output over 12 hours were collected and assayed for intact didanosine by validated HPLC assays. Pharmacokinetic parameters were calculated using noncompartmental methods. The mean parameters are listed below.

| Formulation | CMAX (ng/ml) | TMAX* (hr) | MRT(INF) (hr) | T-HALF (hr) | AUC(INF) (hr.ng/ml) | CLR (ML/min) | % UR |
|---|---|---|---|---|---|---|---|
| C/P Buffer | 1901 | 0.68 | 1.77 | 1.36 | 2851 | 507 | 21.9 |
| Chewable Tablet | 2364 | 0.50 | 1.86 | 1.37 | 3315 | 455 | 23.0 |
| Suspension | 2651 | 0.50 | 1.80 | 1.39 | 3574 | 477 | 26.4 |

TMAX*: median was reported.
CMAX - highest observed plasma concentration of drug.
TMAX - time elapsed to reach CMAX.
T-HALF - the drug elimination half-life.
AUC(INF) - the are under the drug concentration vs time curve, extrapolated to infinity.
MRT(INF) - mean residence time in the body, extrapolated to infinity.
CLR - renal clearance of drug.
UR - total urinary recovery.

The rate of absorption and elimination of these three formulations were essentially the same, based on the values of TMAX, MRT(INF) and T-HALF. The pharmacokinetic characteristics of didanosine remained unaltered regardless of the differences in formulation. The bioavailability estimates with 90% confidence limits for the chewable tablet relative to the citrate/phosphate buffer were 124% (106–135%) for CMAX and 116% (108–125%) for AUC (INF). The bioavailability estimates with 90% confidence limits for the suspension relative to the citrate/phosphate buffer were 139% (121–154%) for CMAX and 125% (117–134%) for AUC(INF). Based on the 90% confidence interval approach, the two new formulations were more bioavailable than the reference formulation, citrate/phosphate buffer.

EXAMPLE 7

Evaluation of the Comparative Bioavailability of Didanosine (2',3'-Dideoxyinosine, ddI) After Administration as a Solution and as a Chewable Tablet The bioavailability of a chewable tablet formulation of didanosine relative to the reference formulation, a citrate/phosphate buffer sachet, was evaluated in 24 male patients seropositive for the Human Immunodeficiency Virus. Using a randomized crossover study design, a single 375 mg oral dose of the citrate/phosphate buffer sachet or a 300 mg dose of the chewable tablet (administered as 2×150 mg tablets) was given under fasting conditions. The alternate treatment was given 1 week later. Serial blood samples and the total urinary output were collected over a 12 hr interval after each dose. Plasma and urine samples were analyzed for didanosine using validated HPLC/UV methods. Concentration data were used to calculate pharmacokinetic parameters using noncompartmental methods. Mean (SD) values for key parameters are summarized below.

| Formulation | CMAX (ng/ml) | TMAX* (hr) | MRT(INF) (hr) | T-HALF (hr) | AUC(INF) (hr.ng/ml) | CLR (ML/min) | % UR |
|---|---|---|---|---|---|---|---|
| Citrate/Phosphate | 1595 (584) | 0.75 | 2.35 (0.79) | 1.76 (0.82) | 2953 (838) | 469 (160) | 78.4 (26.7) |
| Chewable Tablet | 1628 (548) | 0.50 | 2.18 (0.59) | 1.73 (1.03) | 2571 (773) | 433 (169) | 64.2 (25.4) |

TMAX*: median was reported.

There were no statistically significant sequence or period effects observed for any parameter, based on analysis of variance results. The bioavailability assessment of the chewable tablet formulation of didanosine relative to the citrate/phosphate buffer was made on the basis of the two one-sided tests procedure. The point estimate and 90% confidence interval for CMAX for the chewable tablet relative to the citrate/phosphate buffer sachet was 103% (95%, 112%). Corresponding values for AUC/INF) were 87% (81%, 93%). It is concluded that a 375 mg dose of didanosine, administered as the citrate/phosphate buffer is equivalent to a 300 mg dose of the chewable tablet.

EXAMPLE 8

Didanosine Chewable/Dispersible Buffered Tablets

The following tablet formulations are made using the procedures outlined above. These formulations have been utilized in clinical practice for efficacy studies. All of these tablets are qualitatively similar having the same physical parameters.

|  | Strength | | | | | |
|---|---|---|---|---|---|---|
| Ingredients | Placebo | 25 mg | 50 mg | 100 mg | 150 mg | 200 mg |
| Didanosine activity | — | 0.25 | 0.050 | 0.100 | 0.150 | 0.200 |
| Calcium carbonate | 0.550 | 0.550 | 0.550 | 0.550 | 0.550 | 0.550 |
| Magnesium hydroxide | 0.250 | 0.250 | 0.250 | 0.250 | 0.250 | 0.250 |
| Aspartame | 0.065 | 0.065 | 0.065 | 0.065 | 0.065 | 0.065 |
| Sorbitol 30/60 DC | 0.350 | 0.342 | 0.333 | 0.316 | 0.300 | 0.280 |
| Microcrystalline cellulose | 0.700 | 0.683 | 0.667 | 0.634 | 0.600 | 0.570 |
| Polyplasdone XL-10 | 0.100 | 0.100 | 0.100 | 0.100 | 0.100 | 0.100 |
| Mandarin orange | 0.050 | 0.050 | 0.050 | 0.050 | 0.050 | 0.050 |
| Magnesium stearate (slugging) | 0.015 | 0.015 | 0.015 | 0.015 | 0.015 | 0.015 |
| Magnesium stearate (tabletting) | 0.020 | 0.020 | 0.020 | 0.020 | 0.020 | 0.020 |
| Net Tablet weight(g) | 2.100 | 2.100 | 2.100 | 2.100 | 2.100 | 2.100 |

As the tablet potency is increased with added didanosine, an equal reduction in the combined weight of microcrystalline cellulose and sorbitol is made to adjust for constant tablet weight. The ratio of microcrystalline cellulose to sorbitol is kept at a 2:1 ratio for all tablet strengths.

EXAMPLE 9

In-Vitro Testing of Stability of ddI (Stomach Degradation Model)

Didanosine (2,3-dideoxyinosine, dideoxyinosine, ddI) is an antiviral compound which demonstrates activity against the human immunodeficiency virus (HIV). This compound is presently indicated as a clinical agent for the treatment of Acquired Immune Deficiency Syndrome (AIDS). This compound is highly acid labile, but is quite stable in an alkaline environment {e.g., $t_{90}$ (time period in which 90% of drug disappears) at 37° C. is <2 minutes at pH <3, 16 days at pH 7.4, and 509 days at pH 9.5 (1–3)}. While didanosine had been available previously in the form of a lyophilized intravenous dosage form, an oral dosage form is preferred for long-term therapy.

The acid labile nature of the didanosine bulk drug requires that the developed oral dosage form protect didanosine from acid degradation in the stomach after oral administration. The required degree of protection depends on the amount of residual acid in the stomach, the acid secretion rate, the gastric emptying rate for the dosage form, and the minimum gastric pH for acceptable didanosine stability.

Table 2 summarizes literature reporting human adult gastric secretion characteristics. These data suggest that the selected formulation should be capable of neutralizing a minimum of 27 mEq acid in an hour, assuming that the drug is administered on an empty stomach.

TABLE 2

Adult Human Stomach pH and Acid Secretion Characteristics*

| | |
|---|---|
| Stomach pH at Rest | 1–2 |
| Maximum Residual Acid at Rest | 4 mEq |
| Maximum Secretion Rate at Rest | 5 mEq/hour |
| Maximum Secretion Rate with Food | 40 mEq/hour |
| Mean of Max. Secretion Rates at Rest and with Food | 23 mEq/hour |

*Modified from: L.R. Johnson, "Gastric Secretion," Gastrointestinal Physiology, L. R. Johnson, Ed., The C. V. Mosby Co., St. Louis, MO, 2nd ed. 1981, p. 70.

The literature indicates that, in most cases, solutions empty from the human stomach within ½ hour under fasting conditions. In order to provide optimum bioavailability, the developed formulation should protect didanosine from an acidic environment for at least ½ hour.

Using the Acid Neutralization Rate Test (Example 1), solution stability of didanosine as a function of pH, in the range of pH 3–5, was determined at 37° C. The data are presented in FIG. 1. These data indicate a significant increase in the degradation rate as the solution pH was reduced. Less than 4% didanosine degradation was observed in ½ hour at pH 5. Thus, pH 5 was selected as the minimum pH which the formulation should maintain for at least ½ hour in the acid neutralization rate test described above.

The ideal buffer should maintain stomach pH above 5 for approximately one hour. However, the developed buffer should not raise the stomach pH much above 5, so as not to create a physiological pH imbalance in the gastrointestinal tract.

We claim:

1. A pharmaceutical composition for oral delivery of dideoxypurine nucleosides with improved bioavailability, the composition comprising;

from about 5 to 375 mg per dosing unit of a dideoxy purine nucleoside selected from the group consisting of 2',3'-dideoxyadenosine (ddA), 2',3'-dideoxyinosine (ddI), 2',3'-dideoxyguanosine (ddG), and individual pharmaceutically acceptable salts, prodrug esters, and hydrates thereof;

and about 800 to 2800 mg of a water-insoluble antacid buffering composition which contains a water insoluble antacid magnesium compound selected from the group consisting of magnesium carbonate, magnesium carbonate hydroxide, magnesium hydroxide, magnesium oxide, magnesium (tribasic) phosphate and magnesium trisilicate, combined with a dihydroxyaluminum alkali metal carbonate or with calcium carbonate;

optionally containing a soluble citrate buffer;

and which optionally additionally contains binders, disintegrants, sweeteners, flavoring agents, and other pharmaceutically acceptable excipients;

with the proviso that the formulation does not act like a bulk laxative, cause constipation, or cause either physiological pH or electrolyte imbalances in the host following administration.

2. The pharmaceutical composition of claim 1 wherein the water-insoluble antacid buffering composition contains one part of a water-insoluble antacid magnesium compound in combination with about 2 to 4 parts of a dihydroxyaluminum alkali metal carbonate or with about 1.5 to 3 parts of calcium carbonate.

3. A chewable oral tablet formulation that may chewed or dispersed in a liquid and swallowed, the tablet formulation containing the pharmaceutical composition of claim 1.

4. The composition of claim 1 containing a sweetening agent.

5. The composition of claim 4 wherein the sweetening agent is selected from the group consisting of aspartame, sorbitol and sucrose.

6. The composition of claim 1 containing a flavoring agent.

7. The composition of claim 1 containing a disintegrant.

8. The composition of claim 1 containing a binder.

9. The composition of claim 1 containing pharmaceutically acceptable excipients.

10. The composition of claim 1 wherein the dideoxy purine nucleoside is ddI.

11. The composition of claim 1 wherein the water-insoluble antacid buffering composition contains a dihydroxyaluminum alkali metal carbonate.

12. The composition of claim 11 wherein the water-insoluble antacid buffering composition contains dihydroxyaluminum sodium carbonate.

13. The composition of claim 1 wherein the water-insoluble antacid buffering composition contains calcium carbonate.

14. The composition of claim 1 wherein the water-insoluble antacid magnesium compound is magnesium hydroxide.

15. The composition of claim 1 containing -ddI, dihydroxyaluminum sodium carbonate, magnesium hydroxide, a soluble citrate antacid buffer, a sweetening agent, and a flavoring agent.

16. The composition of claim 1 containing -ddI, calcium carbonate, magnesium hydroxide, a sweetening agent, and a flavoring agent.

17. An oral tablet formulation containing the pharmaceutical composition of claim 15.

18. An oral tablet formulation containing the pharmaceutical composition of claim 16.

19. An oral powder formulation for dispersal in a liquid and containing the pharmaceutical composition of claim 1.

20. An oral powder formulation for dispersal in a liquid and containing the pharmaceutical composition of claim 15.

21. An oral powder formulation for dispersal in a liquid and containing the pharmaceutical composition of claim 16.

22. A chewable or dispersible tablet formulation comprising from about 5 to 375 mg of ddI; about 1.3 to 1.4 g of dihydroxyaluminum sodium carbonate; about 0.4 to 0.5 g of magnesium hydroxide; about 0.3 g of sodium citrate dihydrate; about 0.06 g aspartame and about 0.16 g sucrose; about 0.075 g tablet disintegrant, about 0.04 g silicon dioxide; about 0.02 g wintergreen flavor; about 0.05 g magnesium stearate; and sufficient microcrystalline cellulose to yield a tablet weighing about 3.0 g.

23. A chewable or dispersible tablet formulation comprising about 5 to 375 mg of ddI; about 0.5 to 0.6 g calcium carbonate; about 0.2 to 0.3 g magnesium hydroxide; about 0.06 g aspartame; about 0.08 g tablet disintegrant; about 0.02 g silicon dioxide; about 0.05 g orange flavor; about 0.02 g magnesium stearate and sufficient microcrystalline cellulose to yield a tablet weighing about 1.9 g.

24. A chewable or dispersible tablet formulation comprising about 5 to 375 mg of ddI; about 0.5 to 0.6 g calcium carbonate; about 0.2 to 0.3 g magnesium hydroxide; about 0.07 g aspartame; about 0.1 g tablet disintegrant; about 0.3 g sorbitol; about 0.05 g mandarin orange flavor; about 0.03 g magnesium stearate and sufficient microcrystalline cellulose to yield a tablet weighing about 2.1 g.

* * * * *